(12) United States Patent
Peacock et al.

(10) Patent No.: US 9,772,271 B2
(45) Date of Patent: Sep. 26, 2017

(54) APPARATUS FOR TESTING A FILTER

(75) Inventors: Ryan Val Peacock, Baltimore, MD (US); Donald Jonathan Largent, Hampstead, MD (US); Sylvain Dominique Masset, Reisterstown, MD (US)

(73) Assignee: HAMILTON ASSOCIATES, INC., Owings Mills, MD (US)

( * ) Notice: Subject to any disclaimer, the term of this patent is extended or adjusted under 35 U.S.C. 154(b) by 1242 days.

(21) Appl. No.: 13/507,321

(22) Filed: Jun. 21, 2012

(65) Prior Publication Data
US 2013/0340501 A1    Dec. 26, 2013

(51) Int. Cl.
*G01N 15/06* (2006.01)

(52) U.S. Cl.
CPC ..... *G01N 15/06* (2013.01); *G01N 2015/0662* (2013.01)

(58) Field of Classification Search
CPC  B01D 46/446; B01D 46/444; B01D 2273/18; B01D 46/44; G01N 2001/2223; G01N 2015/084
See application file for complete search history.

(56) References Cited

U.S. PATENT DOCUMENTS

| | | | |
|---|---|---|---|
| 3,587,323 A * | 6/1971 | Benjaminson et al. ............ | G01N 1/2273 73/863.21 |
| 4,220,621 A * | 9/1980 | Simpson .................. | G01N 1/38 422/63 |
| 4,361,027 A | 11/1982 | Schmitt | |
| 4,478,096 A * | 10/1984 | Heiland ................... | G01N 1/24 73/40.7 |
| 4,494,403 A * | 1/1985 | Bowers ............. | B01D 46/0006 73/40.7 |
| RE31,952 E * | 7/1985 | Wilcox ............. | B01D 46/0004 239/514 |
| 4,718,268 A * | 1/1988 | Reid ..................... | G01V 9/007 73/19.01 |

(Continued)

FOREIGN PATENT DOCUMENTS

CA    2345631 A1 *  11/2001  ............. D06F 58/28

OTHER PUBLICATIONS

"SP200DAS Aerosol Photometer", DOP Solutions Ltd, pp. 1-2.
(Continued)

*Primary Examiner* — David A Rogers
(74) *Attorney, Agent, or Firm* — Merek, Blackmon & Voorhees, LLC

(57) ABSTRACT

A preferred form of the invention is directed to a system and method used to test filters. The system preferably includes a base unit and a probe operably associated with the base unit. The probe is configured to be deployed adjacent the filter being tested while the filter is located in an operating position. The probe is further configured to allow an operator to vary the mode of operation of the base unit from the probe. The system is configured to automatically exhaust any residual test sample from the base unit and the probe when the system changes between testing a sample upstream and downstream of the filter. The system further includes noise suppression on at least one of the upstream test sample and downstream test sample. The system further is configured to detect when the probe is connected to the base unit.

21 Claims, 13 Drawing Sheets

(56) References Cited

U.S. PATENT DOCUMENTS

| | | | |
|---|---|---|---|
| 4,876,902 A * | 10/1989 | von Alfthan | G01N 1/14 73/863.83 |
| 4,942,774 A * | 7/1990 | McFarland | G01N 1/2247 73/863.51 |
| 5,090,257 A * | 2/1992 | Bruce | G01N 1/2247 73/863.03 |
| 5,107,713 A | 4/1992 | Peck et al. | |
| 5,269,659 A | 12/1993 | Hampton et al. | |
| 5,295,790 A | 3/1994 | Bossart et al. | |
| 5,345,809 A | 9/1994 | Corrigan et al. | |
| 5,356,594 A * | 10/1994 | Neel | G01M 3/20 422/54 |
| 5,554,846 A | 9/1996 | Regiec et al. | |
| 5,578,834 A * | 11/1996 | Trobridge | G01N 21/3504 250/551 |
| 5,608,647 A | 3/1997 | Rubsamen et al. | |
| 5,993,743 A * | 11/1999 | Nordman | G01N 1/2252 250/339.13 |
| 5,996,422 A | 12/1999 | Buck et al. | |
| 6,092,992 A | 7/2000 | Imblum et al. | |
| 6,360,085 B1 * | 3/2002 | Walley | H04B 1/1027 455/226.2 |
| 6,378,385 B1 * | 4/2002 | Bowers | G01N 1/22 73/863.12 |
| 6,418,783 B2 | 7/2002 | Sunshine et al. | |
| 6,553,848 B1 * | 4/2003 | Tallentire | G01N 1/2247 73/863.41 |
| 6,829,551 B2 | 12/2004 | Von Der Hardt et al. | |
| 6,865,940 B2 * | 3/2005 | Poole | G01N 27/223 73/29.01 |
| 6,955,075 B2 * | 10/2005 | Carlson | B03C 3/32 73/28.02 |
| 6,981,402 B2 | 1/2006 | Bristol | |
| 7,010,960 B1 * | 3/2006 | Grantham | G01M 3/00 73/40 |
| 7,022,993 B1 * | 4/2006 | Williams, II | G01M 3/047 250/343 |
| 7,083,392 B2 | 8/2006 | Meza et al. | |
| 7,185,528 B2 | 3/2007 | Bristol | |
| 7,246,515 B2 | 7/2007 | Tyrell | |
| 7,530,352 B2 | 5/2009 | Childers et al. | |
| 7,552,621 B2 * | 6/2009 | Morse | B01D 46/0086 73/38 |
| 7,588,726 B1 * | 9/2009 | Mouradian | G01N 1/2205 422/83 |
| 7,658,787 B2 * | 2/2010 | Morse | B01D 46/0086 55/385.2 |
| 7,669,490 B2 * | 3/2010 | Yoshitome | F24F 3/161 210/85 |
| 7,717,000 B2 | 5/2010 | Xie et al. | |
| 7,739,926 B2 * | 6/2010 | Morse | B01D 46/0086 73/40.7 |
| 7,752,929 B2 | 7/2010 | Kurz | |
| 7,758,664 B2 * | 7/2010 | Morse | B01D 46/0091 454/187 |
| 7,882,727 B2 * | 2/2011 | Morse | B01D 46/0086 73/38 |
| 7,937,987 B2 | 5/2011 | Lowery | |
| 8,021,469 B2 | 9/2011 | Niezgoda et al. | |
| 8,181,544 B2 * | 5/2012 | Crosson | B01B 1/005 702/100 |
| 8,210,056 B2 * | 7/2012 | Pike | B01D 46/002 73/863 |
| 8,307,724 B1 * | 11/2012 | Wichert | G01N 1/24 73/863 |
| 8,372,186 B2 * | 2/2013 | Dobbyn | B08B 15/023 73/863.21 |
| 8,549,895 B2 * | 10/2013 | Chung | B01D 46/442 73/40 |
| 8,567,266 B2 * | 10/2013 | Kaminski | G01N 1/2205 73/863.41 |
| 8,641,617 B2 * | 2/2014 | Natarajan | A61B 5/026 374/110 |
| 8,754,861 B2 * | 6/2014 | Paul | G06F 3/04883 345/173 |
| 9,569,089 B2 * | 2/2017 | Ording | G06F 3/04845 |
| 2002/0112550 A1 * | 8/2002 | Lawless | G01N 1/2273 73/863.21 |
| 2004/0069046 A1 * | 4/2004 | Sunshine | G01N 33/0031 73/23.34 |
| 2006/0042359 A1 * | 3/2006 | Morse | G01M 3/3281 73/40 |
| 2006/0220886 A1 * | 10/2006 | Robertson | G08B 17/10 340/577 |
| 2006/0272301 A1 * | 12/2006 | Morse | B01D 46/0086 55/439 |
| 2007/0068284 A1 * | 3/2007 | Castro | G01N 1/2205 73/863.21 |
| 2007/0214870 A1 * | 9/2007 | Morse | B01D 46/0086 73/37 |
| 2008/0229805 A1 * | 9/2008 | Barket | G01N 1/2214 73/31.01 |
| 2009/0000404 A1 * | 1/2009 | Briscoe | G01N 33/0004 73/864.34 |
| 2009/0107228 A1 * | 4/2009 | Ridley | G01M 17/02 73/146 |
| 2009/0249895 A1 * | 10/2009 | Mahler | B01D 46/0086 73/863.23 |
| 2009/0268201 A1 * | 10/2009 | Call | G01N 15/0625 356/338 |
| 2010/0043409 A1 | 2/2010 | Naydenov et al. | |
| 2010/0097057 A1 | 4/2010 | Karpen | |
| 2010/0154513 A1 | 6/2010 | Lin et al. | |
| 2010/0180699 A1 * | 7/2010 | Bradley | G01N 1/02 73/864.34 |
| 2011/0107819 A1 * | 5/2011 | Chung | B01D 46/442 73/40.7 |
| 2011/0277564 A1 * | 11/2011 | Scott | G01N 1/2214 73/863.23 |
| 2011/0283776 A1 * | 11/2011 | Wu | G01N 1/14 73/31.05 |
| 2012/0137792 A1 * | 6/2012 | Bunker | B08B 7/0092 73/863.22 |
| 2013/0192344 A1 * | 8/2013 | Bryan | B01D 65/102 73/38 |
| 2014/0061449 A1 * | 3/2014 | Tunheim | G01J 3/0218 250/227.11 |

OTHER PUBLICATIONS

"Filter Test Equipment Acc. ISO 14644-3", Lighthouse Worldwide Solutions Benelux BV (Advertisement for DOP Solutions SP200DAS Aerosol Photometer), one page.

"Aerosol Photometer Models 2H and 2HN—Instruction Manual", Air Techniques International, Feb. 2008.

2H Photometer—schematics and drawings, thirty-five (35) pages, Jan. 6, 2003.

2HA Photometer—schematics and drawings, twenty-eight (28) pages, Feb. 2008.

"Aerosol Photometer Models 2H and 2HN—Instruction Manual", Air Techniques International, Feb. 2008, twenty-sight (28) pages.

"Aerosol Photometer Models 2H and 2HN—Instruction Manual", Air Techniques International, May 2014, fifty-four (54) pages.

* cited by examiner

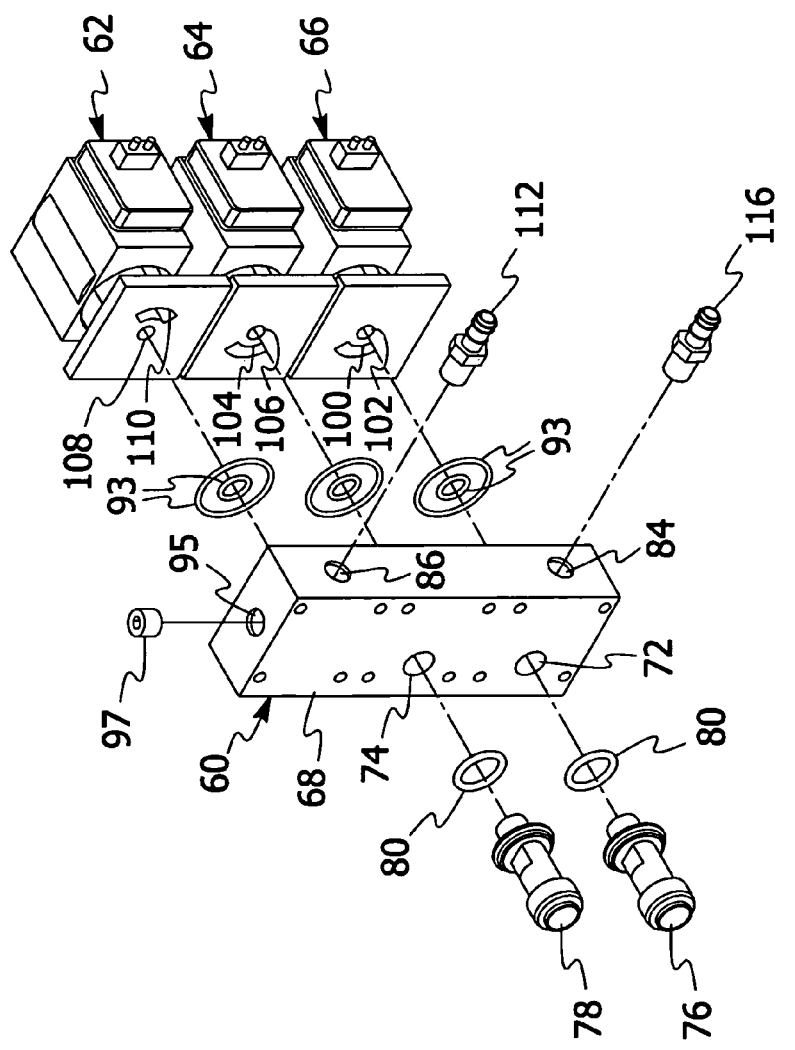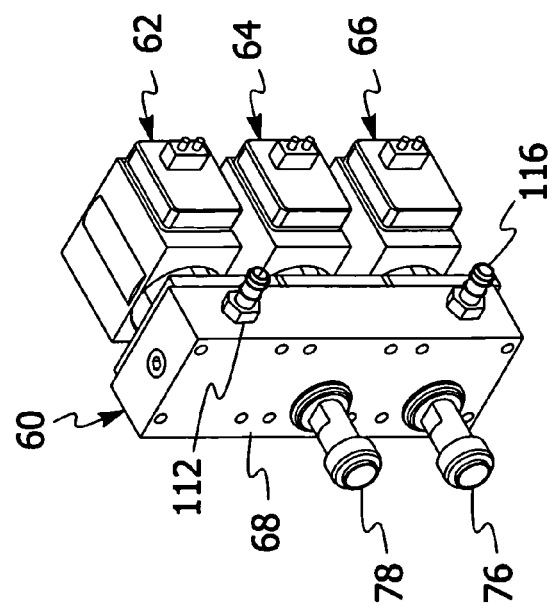

APPARATUS FOR TESTING A FILTER

FIELD OF THE INVENTION

The preferred form of the present invention is directed to an apparatus and method for testing a filter. In the most preferred form, the present invention is directed to an apparatus and method for testing a filter in situ, i.e., the normal operating position of the filter.

BACKGROUND OF THE INVENTION

Various devices have been used to test leakage of various filters employed in bio safety cabinets, pharmaceutical clean rooms, animal testing laboratories and nuclear environments. These devices have included photometers used in conjunction with aerosol generators to measure how well a filter is performing. Typically, an aerosol with a known concentration is introduced before or upstream of the filter and the photometer is operably connected to the downstream side of the filter to measure any leakage of the aerosol through the filter. Photometers typically utilize forward light scattering to measure any leakage of aerosol through the filter being tested.

Prior known devices can test both upstream and downstream samples. To test the upstream sample, a conduit is typically connected to a base unit with the open end of the conduit deployed upstream of the filter being tested. To test the downstream sample, prior known devices have used a probe operably connected to the base unit. The probe is deployed on the downstream side of the filter and conveys the test sample back to the base unit to be processed to determine any leakage of aerosol through the filter.

Prior known systems have several significant limitations. One such drawback is the inability of the prior known devices to change the mode of operation of the testing system without directly interacting with the base unit. For example, the test system cannot be changed between upstream sampling and downstream sampling without manipulating controls located on the base unit. Also, prior known systems do not allow an operator to enter information regarding a filter being tested from a location remote from the base unit. Further, prior known devices do not allow the testing unit to readily test a filter where the test sample (typically aerosol) was unstable. Further, prior known systems do not permit a residual test sample located in the probe and/or base unit to be automatically exhausted when the testing system changes between testing an upstream sample and downstream sample. Moreover, prior known systems have not been configured to detect when the probe is connected to the base unit and alter the operating capabilities of the testing system when the probe is connected to the base unit.

OBJECTS AND SUMMARY OF THE INVENTION

An object of a preferred embodiment of the present invention is to provide a novel and unobvious apparatus and/or process for testing filters.

Another object of a preferred embodiment of the present invention is to provide an apparatus for testing a filter in situ, i.e., the normal operating position of the filter.

A further object of a preferred embodiment of the present invention is to provide an apparatus for testing a filter including a base unit and a probe operably associated with the base unit that allows an operator to readily change the mode of operation without the operator physically manipulating any controls located on the base unit.

Still another object of a preferred embodiment of the present invention is provide an apparatus for testing a filter including a base unit and a probe operably associated with the base unit that allows an operator located adjacent the filter being tested to readily change the mode of operation of the apparatus from the probe.

Still a further object of a preferred embodiment of the present invention is provide an apparatus for testing a filter that automatically exhausts a test sample from a probe and a base unit when the mode of operation is changed between testing an upstream sample and a downstream sample.

Yet still a further object of a preferred embodiment of the present invention is to provide a system for testing a filter having a base unit and a probe operably associated with the base unit where the system can readily detect when the probe is connected to the base unit and alter at least one operational characteristic of the base unit when the probe is connected to the base unit.

Yet another object of a preferred embodiment of the present invention is to provide a system for testing a filter that can readily perform signal noise suppression on an upstream test sample and a downstream test sample.

Still a further object of a preferred embodiment of the present invention is to provide a system for testing a filter having a base unit and probe operably connected to the base unit where the system is configured to prevent noise suppression of a downstream test sample when the probe is connected to the base unit.

It must be understood that no one embodiment of the present invention need include all of the aforementioned objects of the present invention. Rather, a given embodiment may include one or none of the aforementioned objects. Accordingly, these objects are not to be used to limit the scope of the claims of the present invention.

In summary, one embodiment of the present invention is directed to an apparatus for testing a filter in situ. The apparatus includes a base unit configured to operate in at least a first mode and a second mode. In the first mode, the base unit is configured to perform a first test. In the second mode, the base unit is configured to operate in a manner different than the first mode. A probe is operably connected to the base unit. The probe is configured to be deployed adjacent the filter being tested while the filter being tested is located in a normal operating position. The probe further is configured to allow a user to change a mode of the base unit between the first mode and the second mode from the probe.

Another embodiment of the present invention is directed to an apparatus for testing a filter in situ. The apparatus includes an in situ filter test unit for analyzing a test sample. The in situ filter test unit is configured to operate in at least a first operating mode and a second operating mode. In the first operating mode, the in situ filter test unit is configured to receive an upstream test sample taken upstream of a filter being tested. In the second operating mode, the in situ filter test unit is configured to receive a downstream test sample taken downstream of a filter being tested. The in situ filter test unit is further configured to analyze at least one of the downstream test sample and the upstream test sample to determine if the filter being tested is operating satisfactorily without removing the filter being tested from a normal operating position. The in situ filter test unit is configured to automatically initiate a clear mode in which residual test sample in the in situ filter test unit is exhausted from the in situ filter test unit when an operating mode of the in situ filter test unit changes.

A further embodiment of the present invention is directed to an apparatus for testing a filter in situ. The apparatus includes an in situ filter test unit for analyzing a test sample. The in situ filter test unit is configured to operate in at least a first operating mode and a second operating mode. In the first operating mode, the base unit is configured to receive an upstream test sample taken upstream of a filter being tested. In the second operating mode, the base unit is configured to receive a downstream test sample taken downstream of a filter being tested. The base unit is further configured to analyze at least one of the downstream test sample and the upstream test sample to determine if the filter being tested is operating satisfactorily without removing the filter being tested from a normal operating position. The in situ filter test unit is configured to allow a user to perform noise suppression on at least one of the downstream test sample and the upstream test sample. The in situ filter test unit is further configured to allow the user to vary noise suppression.

Still another embodiment of the present invention is directed to an apparatus for testing a filter in situ. The apparatus includes a base unit for performing at least one test on a filter without the filter being removed from a normal operating position. A probe is detachably connected to the base unit. The probe is configured to be deployed adjacent the filter being tested while the filter being tested is located in a normal operating position. The apparatus further includes a sensor for detecting whether the probe is connected to the base unit. The base unit is configured such that at least one functional aspect of the base unit is altered upon detection of the probe being connected to the base unit.

BRIEF DESCRIPTION OF THE DRAWINGS

FIG. 9 is an exploded perspective view of the most preferred form of manifold and valve assembly.

FIG. 10 is a perspective view of the most preferred form of manifold and valve assembly.

DETAILED DESCRIPTION OF THE PREFERRED EMBODIMENT OF THE INVENTION

The most preferred form of the invention will now be described with reference to FIGS. 1-15. The appended claims are not limited to the most preferred embodiment and no term used herein is to be given a meaning other than its ordinary meaning unless expressly stated otherwise.

FIGS. 1 Through 15

Referring to FIGS. 1 to 15, the components of the most preferred form of filter testing system for testing filters are illustrated in one of many possible configurations. Preferably, the filter testing system is an in situ filter testing system, i.e., the filter can be tested when located in its normal operating position.

Figure 4:
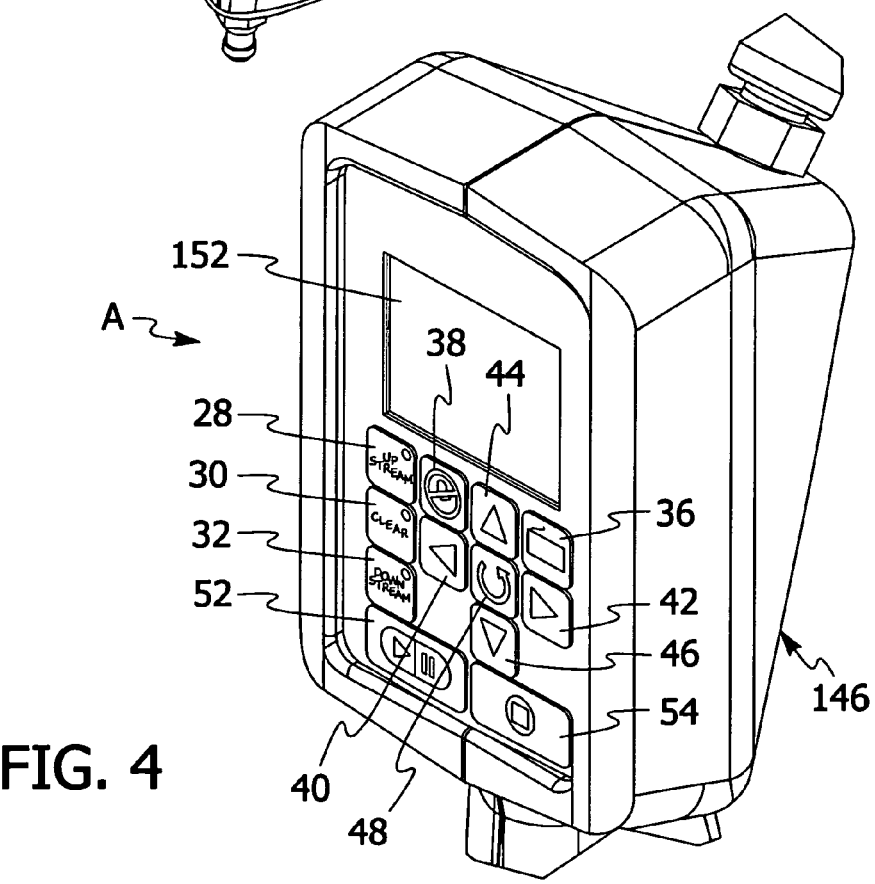
FIG. 4 is a fragmentary perspective view of a portion of the most preferred form of probe depicted in FIG. 1.
Figure 5:
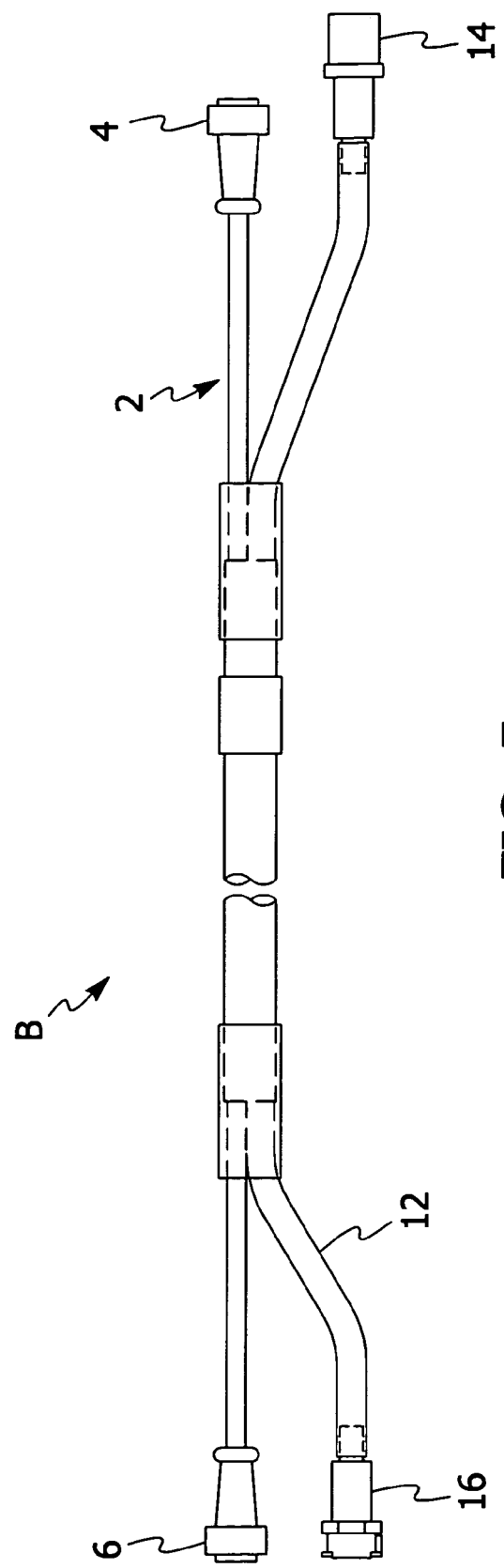
FIG. 5 is a front view of the preferred connector for connecting the probe to a base unit.

The filter testing system preferably includes a probe A (see FIGS. 1 to 4), a coupling assembly B (see FIG. 5) and a base unit C (see FIGS. 6 to 15). The coupling assembly B operably connects the probe A to the base unit C. Referring to FIG. 5, coupling assembly B includes an electrical coupler 2 having electrical connectors 4 and 6 disposed at opposite ends. When probe A is to be used with the base unit C to test a filter, connector 4 is coupled to electrical connection port 8 (see FIG. 6) of base unit C and connector 6 is coupled to electrical connection port 10 (see FIG. 2) of probe A. Coupling assembly C further includes a fluid conduit 12 having connectors or couplers 14 and 16 disposed at opposite ends.

Connector 14 is coupled to downstream test sample port 18 (see FIG. 6) of base unit C while connector 16 is coupled to downstream test sample port 20 (see FIG. 2) of probe A. A conduit (not shown) similar to fluid conduit 12 may be used to convey a test sample (preferably aerosol) upstream of the filter being tested into the base unit C through upstream test sample port 22 for testing of the upstream test sample.

Referring to FIGS. 6 to 8 and 15, base unit C includes a housing 24 having a frame 25, a front panel 26, a rear panel 27, a bottom panel 29 and a cover panel 31. Cover panel 31 preferably includes a handle 33. Referring to FIGS. 6 to 8 and 15, front panel 26, rear panel 27, bottom panel 29 and cover panel 31 are detachably connected to frame 25 by fasteners 35. Housing 24 houses manifold and valve assembly D, dual headed vacuum pump E, vacuum pump power supply F, photometer G, flow meter assembly H, fan I, power entry module J, interface board K, main circuit board L having a microprocessor, clean air filter M and exhaust air filter N.

Figure 6:
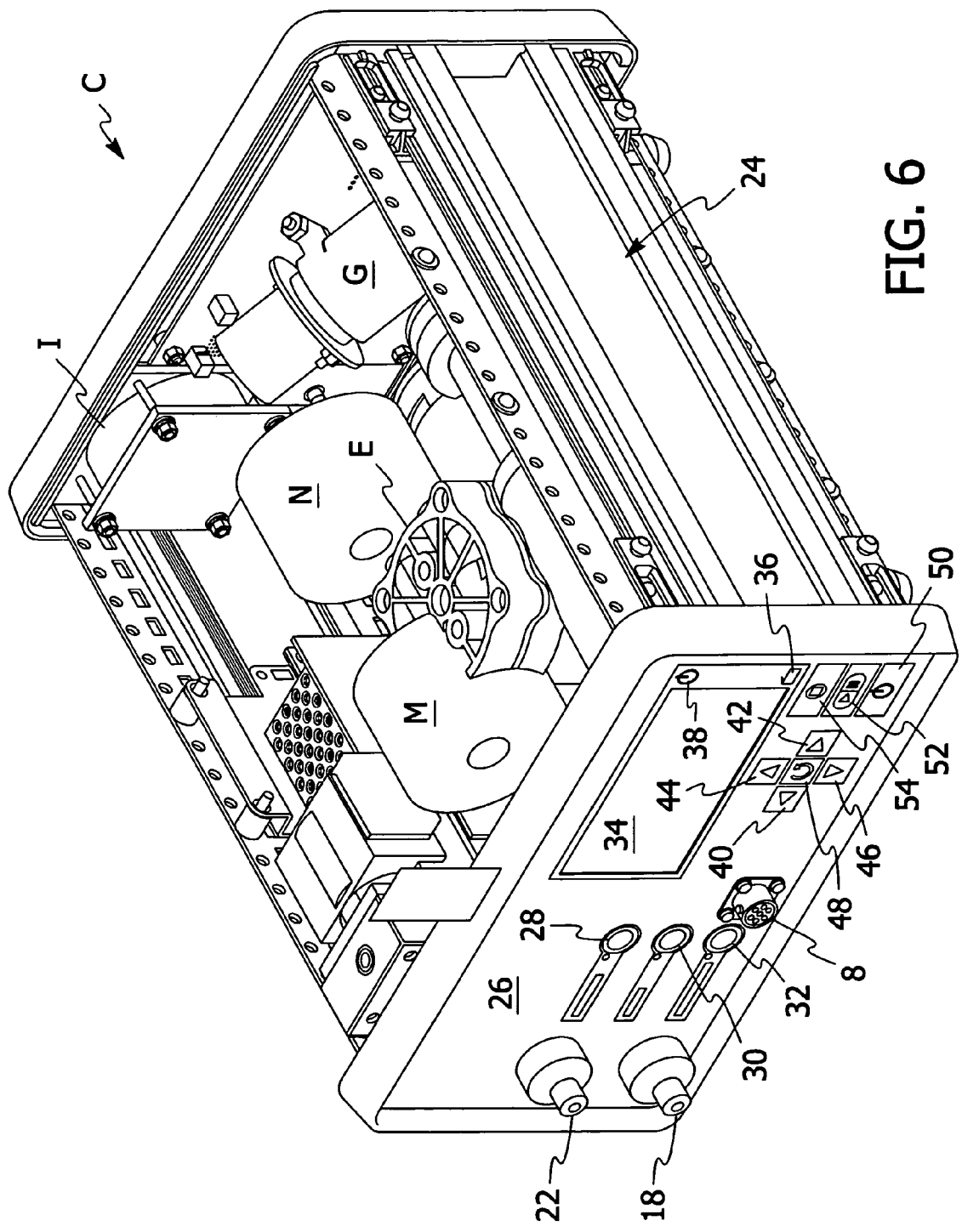
FIG. 6 is a perspective view of the most preferred form of the base unit with a portion of the housing of the base unit removed.
Figure 7:
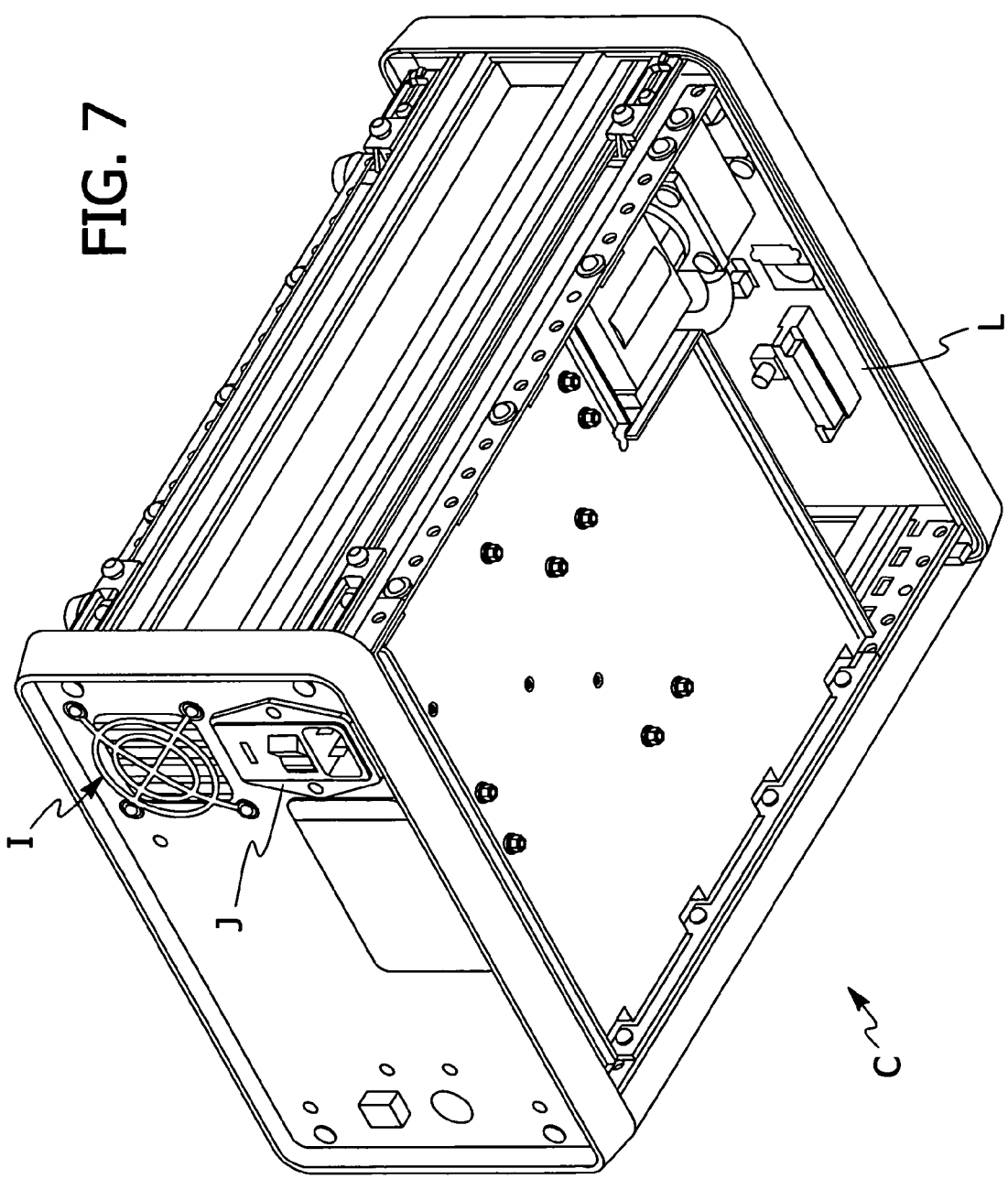
FIG. 7 is another perspective view of the most preferred form of the base unit with a portion of the housing of the base unit removed.

Referring to FIG. 6, electrical connection port 8, downstream test sample port 18 and upstream test sample port 22, extend outwardly from front panel 26. Front panel 26 preferably includes three control members 28, 30 and 32. Base unit C will test an upstream sample when control member 28 is activated by an operator depressing this control member. Base unit C will test a downstream test sample when control member 32 is activated by an operator depressing this control member. When control member 30 is depressed by an operator, residual test samples in the base unit C will be exhausted from the filter testing system as will be explained in more detail below.

Front panel 26 further includes an LCD display screen 34 for displaying the operating menu of the filter testing system as well as the results of the filter test. It will be readily appreciated that the present invention is not limited to an LCD display but rather any suitable vehicle may be used for providing the operator with the desired information regarding the operation of the filter testing system. Front panel 26 also includes control members 36 and 38. Upon depression of control member 36, an alpha-numeric key pad will be displayed on screen 34. Control member 38 allows an operator to disable the audible alarm feature of the filter test system if desired, i.e., by depressing control member 38 the audible alarm that would typically sound when a filter has failed the test will be disabled.

Front panel 26 includes cursor directional control members 40, 42, 44 and 46 which allow an operator to move a cursor left, right, up and down on screen 34, respectively. Control member 48 is also provided on front panel 26. Control member 48 acts as an enter key. Using control members 40 through 48, an operator may readily navigate through the alpha-numeric key board and the menu to enter information regarding a filter being tested or select various features available in the menu.

Front panel 26 further includes control members 50, 52 and 54. Upon depression of control member 50 the base unit will power up. By pressing the arrow portion of control member 52, the filter testing system will perform the test selected by the operator. By pressing the two parallel vertical lines portion of control member 52, the test being performed will be paused. To continue the filter test, the arrow portion of control member is depressed. By depressing control member 54, the test is stopped.

Referring to FIGS. 8, 9, 9A, 9B and 10, manifold and valve assembly D includes a manifold 60 and solenoid valves 62, 64 and 66 operably connected to manifold 60. Manifold 60 includes a front face 68 and a rear face 70. Openings 72 and 74 are formed in front face 68 and receive respectively inlet ports 76 and 78. O-rings 80 provide a fluid tight connection between inlet ports 76 and 78 and manifold 60. Inlet port 76 is connected in a fluid tight manner to downstream test sample port 18. Inlet port 78 is connected in a fluid tight manner to upstream test sample port 22.

Figure 9A:
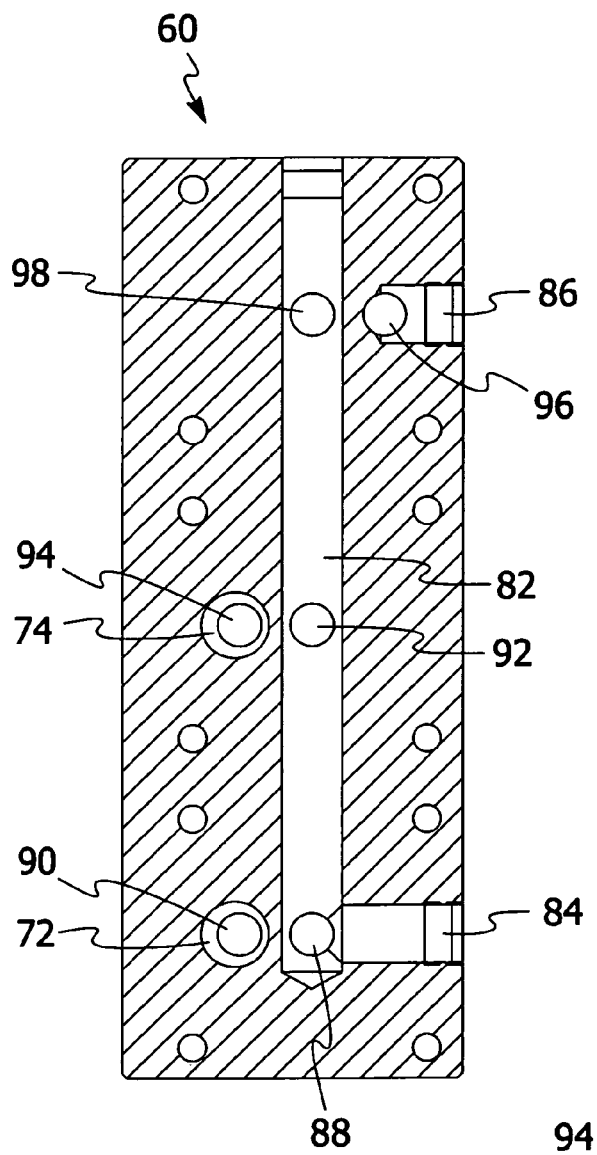
FIG. 9A is a cross-sectional view taken through the mid-section of the most preferred form of manifold.
Figure 9B:
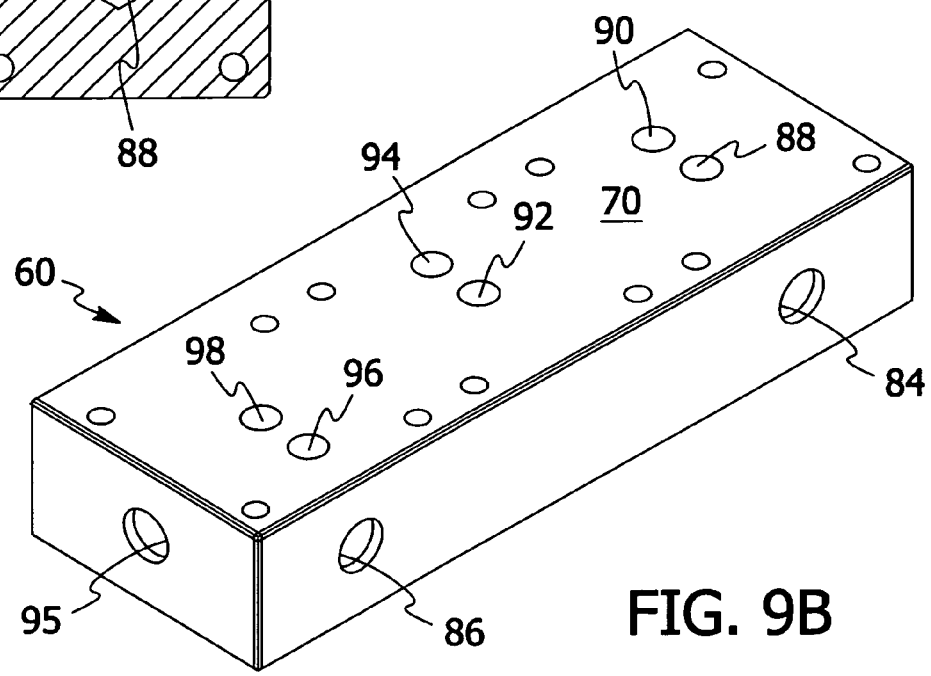
FIG. 9B is a perspective view of the most preferred form of manifold.

Referring to FIG. 9A, manifold 60 includes an internal passageway 82 in fluid communication with test sample exit port or opening 84. Manifold 60 includes clean air entry port 86. Referring to FIG. 9B, rear face 70 of manifold 60 includes openings 88 and 90. Opening 88 is in fluid communication with internal fluid passageway 82. Opening 90 is in fluid communication with opening 72. Rear face 70 also includes openings 92 and 94. Opening 92 is in fluid communication with internal fluid passageway 82. Opening 94 is in fluid communication with opening 74. Rear face 70 further includes openings 96 and 98. Opening 98 is in fluid communication with fluid passageway 82. Opening 96 is in fluid communication with clean air entry port 86. Referring to FIG. 9, opening 95 of manifold 60 is sealed shut by a plug 97.

Solenoid valve 66 is connected in a fluid tight manner to openings 88 and 90 by O-rings 93 such that when solenoid valve 66 is activated, a downstream test sample will flow through the manifold and valve assembly D in the following manner. Referring to FIG. 9, inlet port 76 will receive a downstream test sample from port 18 extending outwardly from front panel 26 of base unit C. The downstream test sample will enter manifold 60 through opening 72 and exit manifold 60 through opening 90. The downstream test sample will in turn enter solenoid valve 66 through passageway 100. The downstream test sample will exit solenoid valve 66 through opening 102 and pass into internal fluid passageway 82 through opening 88. The downstream test sample is discharged from manifold 60 through test sample exit port 84.

Solenoid valve 64 is connected in a fluid tight manner to openings 92 and 94 by O-rings 93 such that when solenoid valve 64 is activated an upstream test sample will flow through manifold and valve assembly D in the following manner. Referring to FIG. 9, inlet port 78 will receive an upstream test sample from port 22 extending outwardly from front panel 26 of base unit C. The upstream test sample will enter manifold 60 through opening 74 and exit manifold 60 through opening 94. The upstream test sample will in turn enter solenoid valve 64 through passageway 104. The upstream test sample will exit solenoid valve 64 through opening 106 and pass into internal fluid passageway 82 through opening 92. The upstream test sample is discharged from manifold 60 through test sample exit port 84.

Solenoid valve 62 is connected in a fluid tight manner to openings 96 and 98 by O-rings 93 such that when solenoid valve 62 is activated clean air will flow through opening 86 and be discharged from manifold 60 through opening 96. The clean air and any residual test sample in manifold 60 will flow into solenoid valve 62 through passageway 108. The clean air and any residual test sample will exit solenoid valve 62 through opening 110 and pass through opening 98 into internal fluid passageway 82 to be discharged from manifold 60 out test sample exit port 84.

Figure 8:
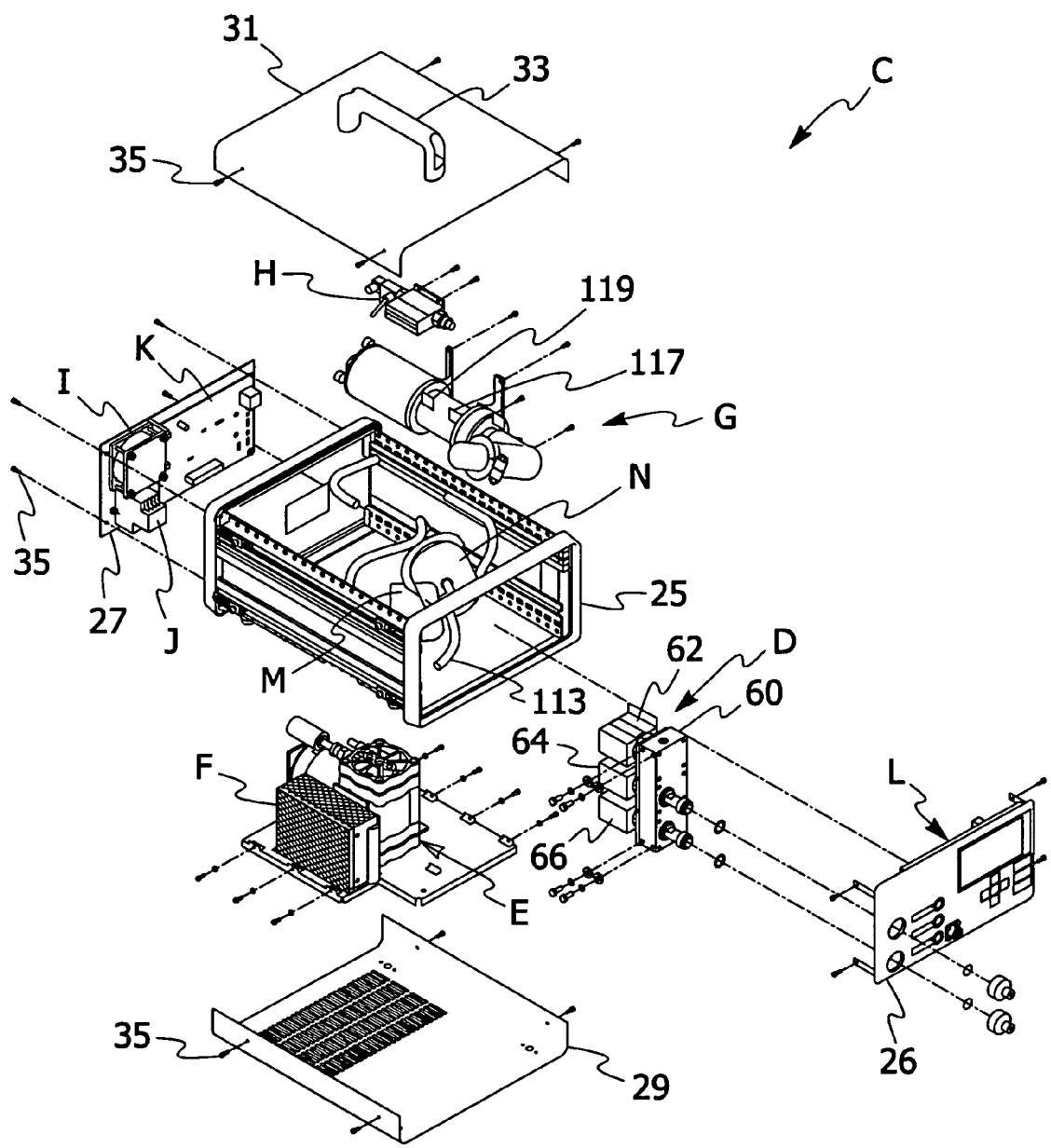
FIG. 8 is an exploded perspective view of the most preferred form of the base unit.

Referring to FIG. 9, a fitting 112 is connected at one end to clean air entry port or opening 86. As seen in FIGS. 6 and 8, flexible tubing 113 connects the other end of fitting 112 to clean air filter M. Fitting 116 is connected to discharge port 84. Flexible tubing extending between fitting 116 and entry port 117 of photometer G directs fluid exiting discharge port 84 into photometer G so that both upstream and downstream test samples may be analyzed to determine the extent of any leakage of the filter being tested. Photometer G is connected to main circuit board L in such a manner as to allow the test results to be displayed on display screen 34. An operator can then enter any desired information about a particular filter being tested through the alpha-numeric key pad. The entered information may be printed out using a printer connected to the base unit at any time after entry. Alternatively, the entered information may be downloaded to any type of temporary or permanent storage device including but not limited to a portable computer (e.g., a lap top) operably connected to base unit C.

Figure 14:
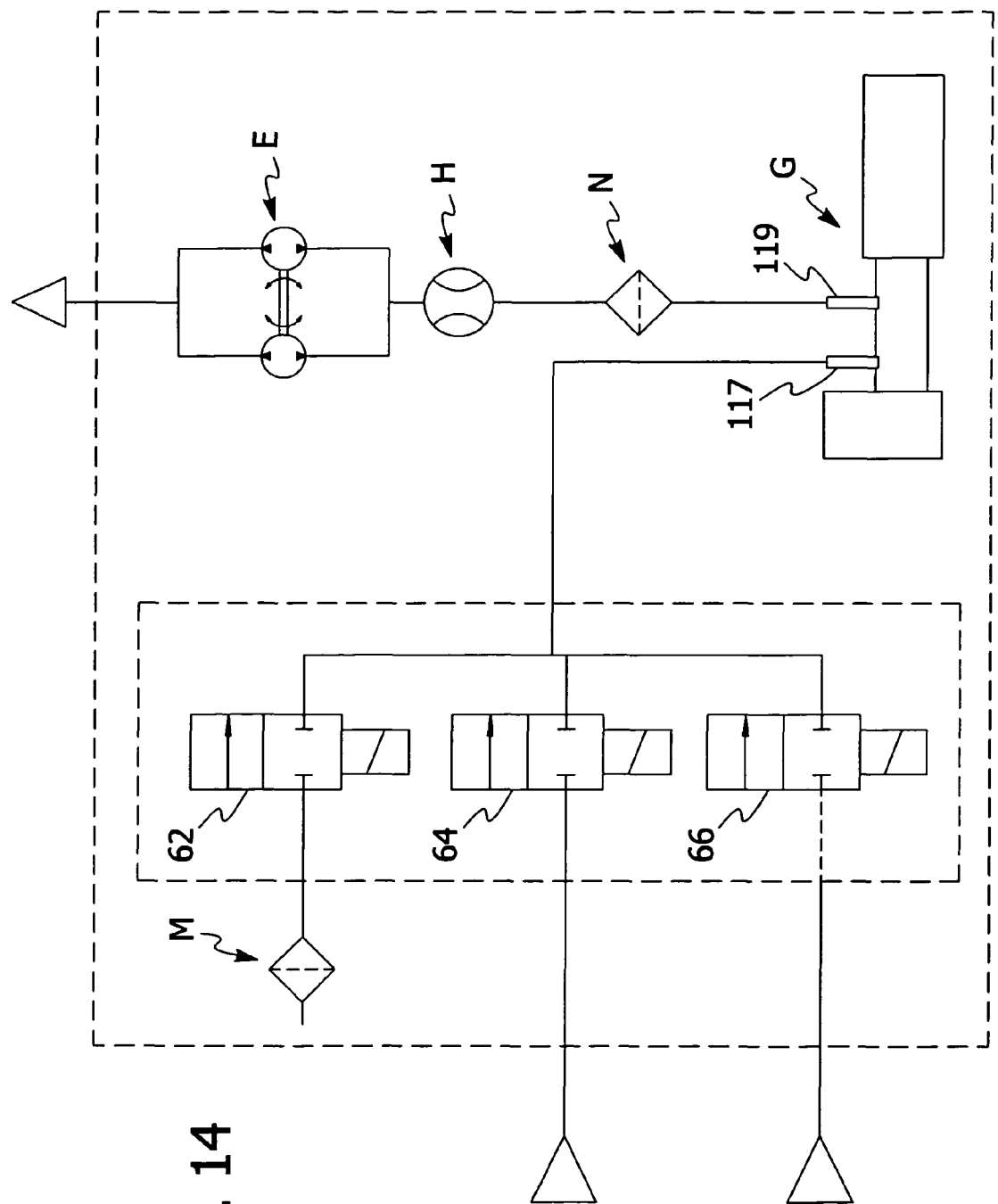
FIG. 14 is a schematic diagram illustrating the operational relationship of various components of the most preferred form of the base unit.

Referring to FIG. 14, the output side or discharge port 119 of photometer G is connected to exhaust filter N, flow meter assembly H and vacuum pump E. Filter N filters out any test sample residue in the air before the air is returned to the room or space adjacent the filter being tested.

Figure 12:
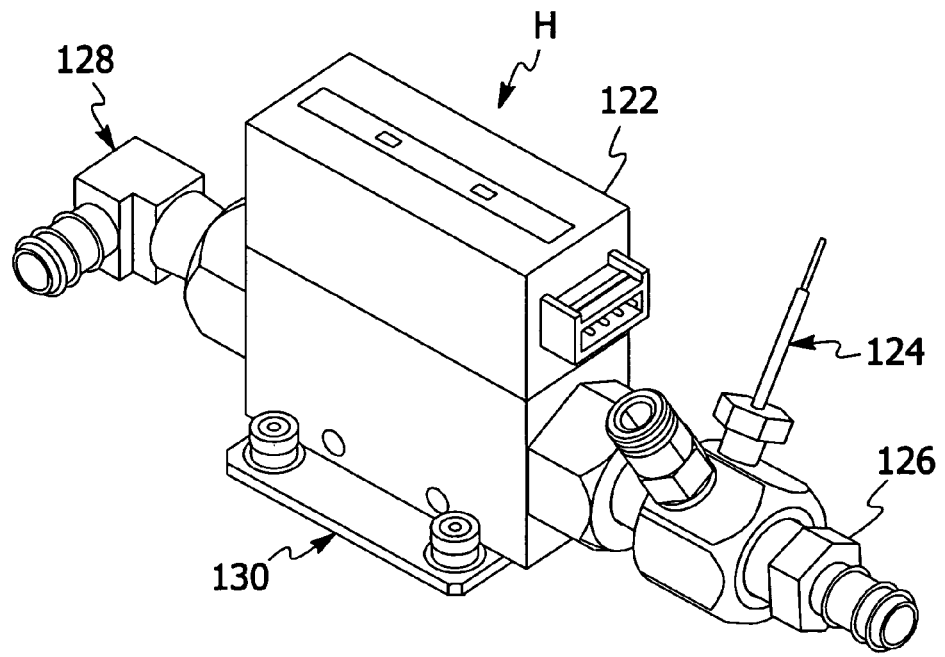
FIG. 12 is a perspective view of the most preferred form of flow meter assembly.
Figure 13:
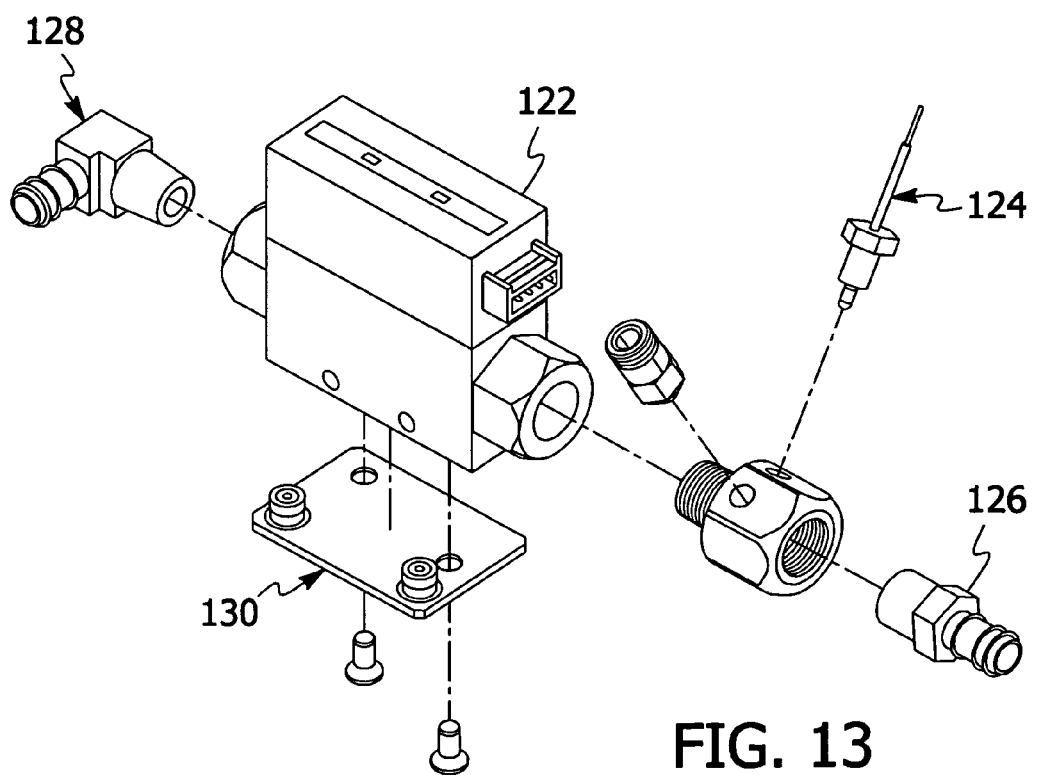
FIG. 13 is an exploded perspective view of the most preferred form of flow meter assembly.
Figure 15:
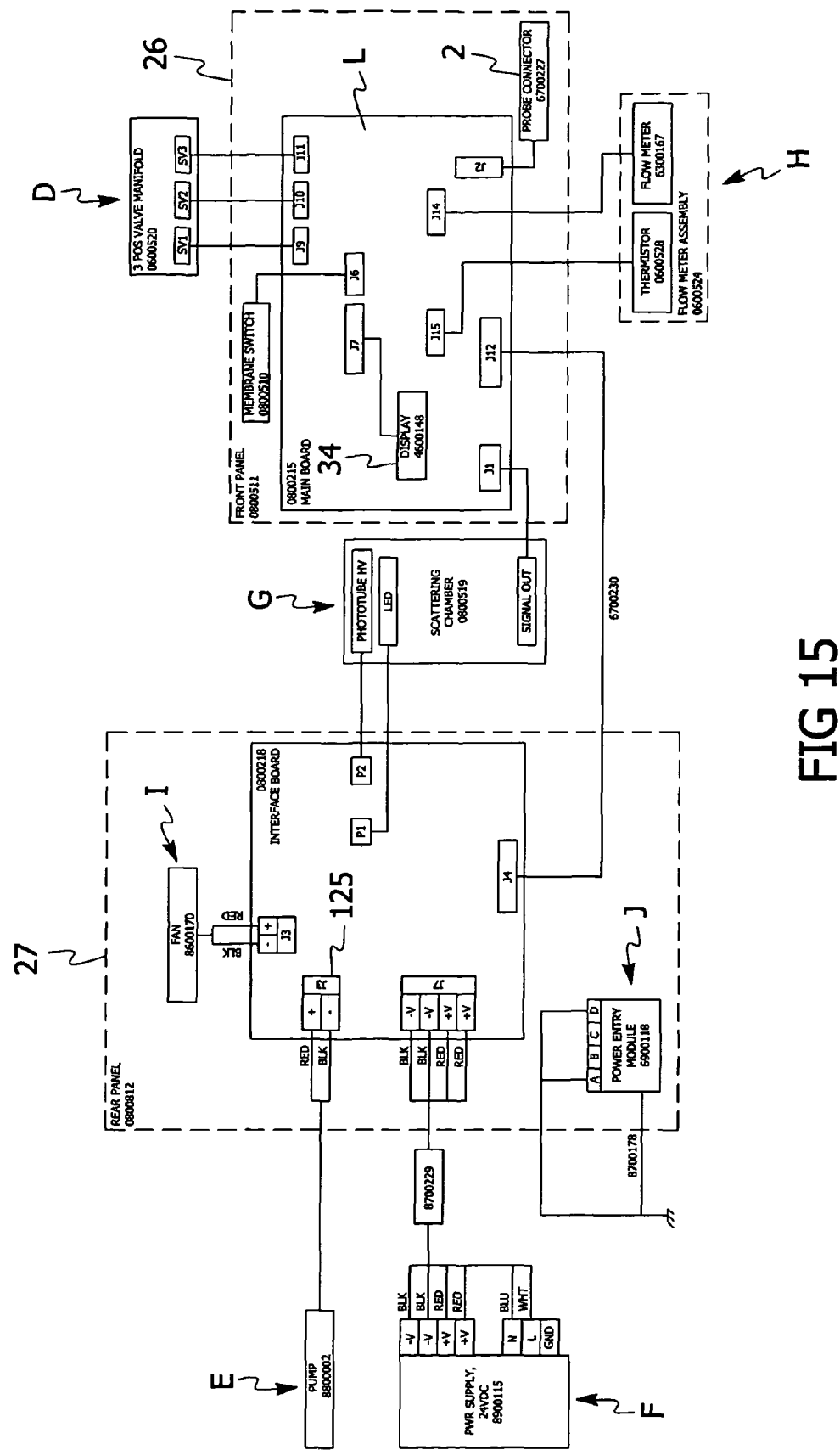
FIG. 15 is a wiring diagram of the most preferred form of the base unit.

Referring to FIGS. 12 and 13, flow meter assembly H includes a flow meter 122, a temperature sensor (e.g., thermistor) 124, input fitting 126, output fitting 128 and mounting bracket 130. Flexible tubing may be used to connect input fitting 126 to the output side of exhaust filter N. Flow meter 122 is preferably a mass flow meter. As seen in FIG. 15, the flow meter assembly H is connected to the main circuit board 124 to permit the microprocessor to determine volumetric flow from the mass flow at a given temperature and pressure. Should the volumetric flow ascertained by the microprocessor be below or above a predetermined operating level, the microprocessor can automatically adjust the power exiting connector 125 on interface board 27 and supplied to vacuum pump E to raise or lower the volumetric flow so that the volumetric flow through base unit C is equal to the predetermined operating level. In this manner, the preferred form of the present invention will readily and automatically compensate for differing atmospheric conditions encountered in different test sites. This feature of a preferred form of the present invention will also readily and automatically compensate for variances in the length of the test sample lines including but not limited to the test sample lines or conduits connecting probe A to base unit C.

Figure 11:
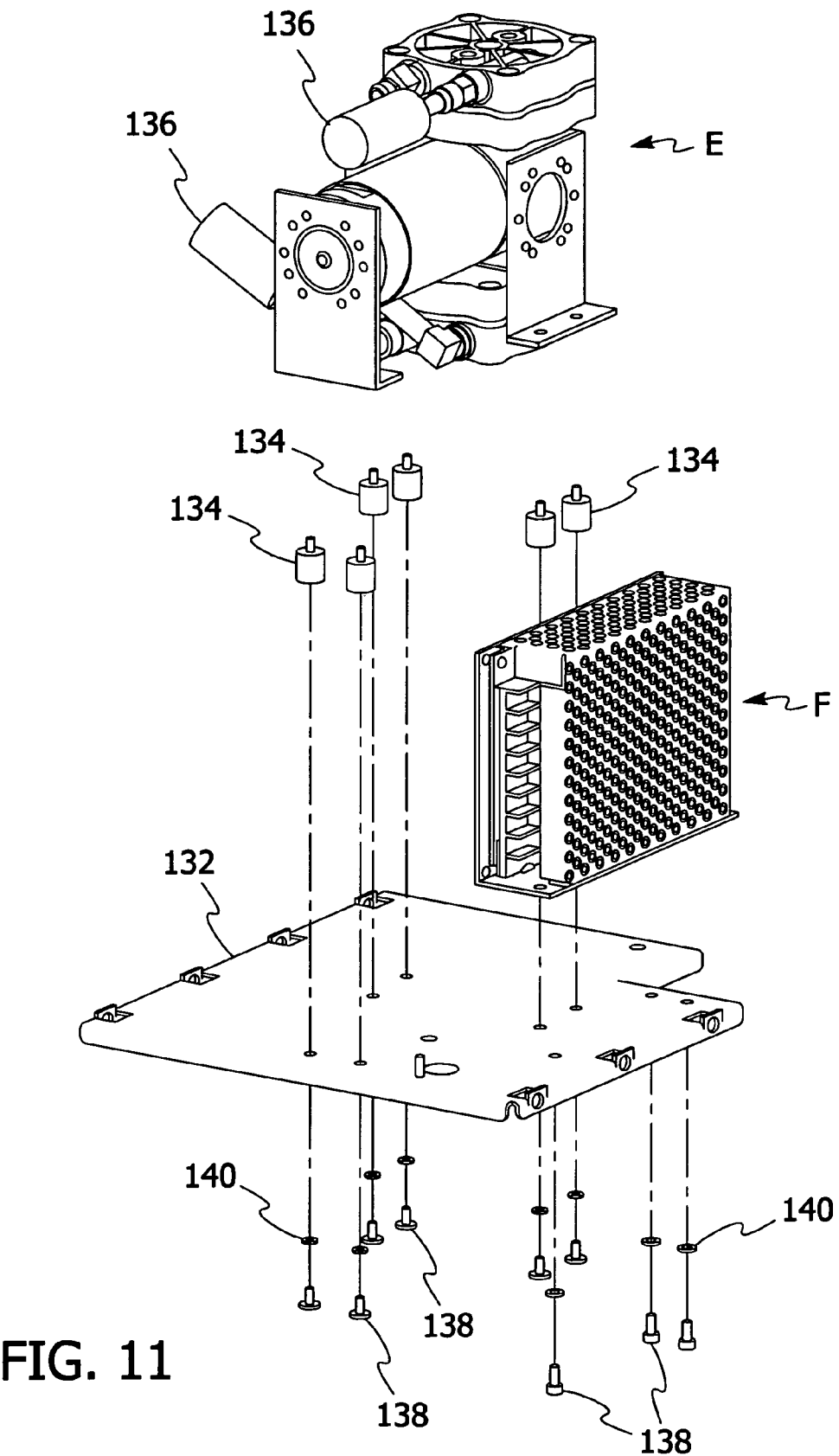
FIG. 11 is an exploded perspective view of the most preferred form of pump, pump power source and mounting plate for the pump and the pump power source.

Referring to FIG. 11, vacuum pump E and power supply F are preferably mounted on a single base plate 132 via shock suppression members 134 which act to isolate vacuum pump E and power supply F from the remaining components of base unit C. Pump E may include silencers 136 to reduce the audible noise produced by pump E. Screws 138 and washers 140 may be used to connect pump E and power supply F to base plate 132.

Referring to FIGS. 1 to 4, probe A includes a test sample collection nozzle or head 142, a hollow, adjustable arm 144, a main body 146 and a handle 148. Arm 144 is in fluid tight communication with nozzle or head 142 and allows an operator to adjust the position of head 142. A conduit 150 (see FIG. 2) connects arm 144 to downstream test sample port 20 extending from the bottom of handle 148.

Figure 1:
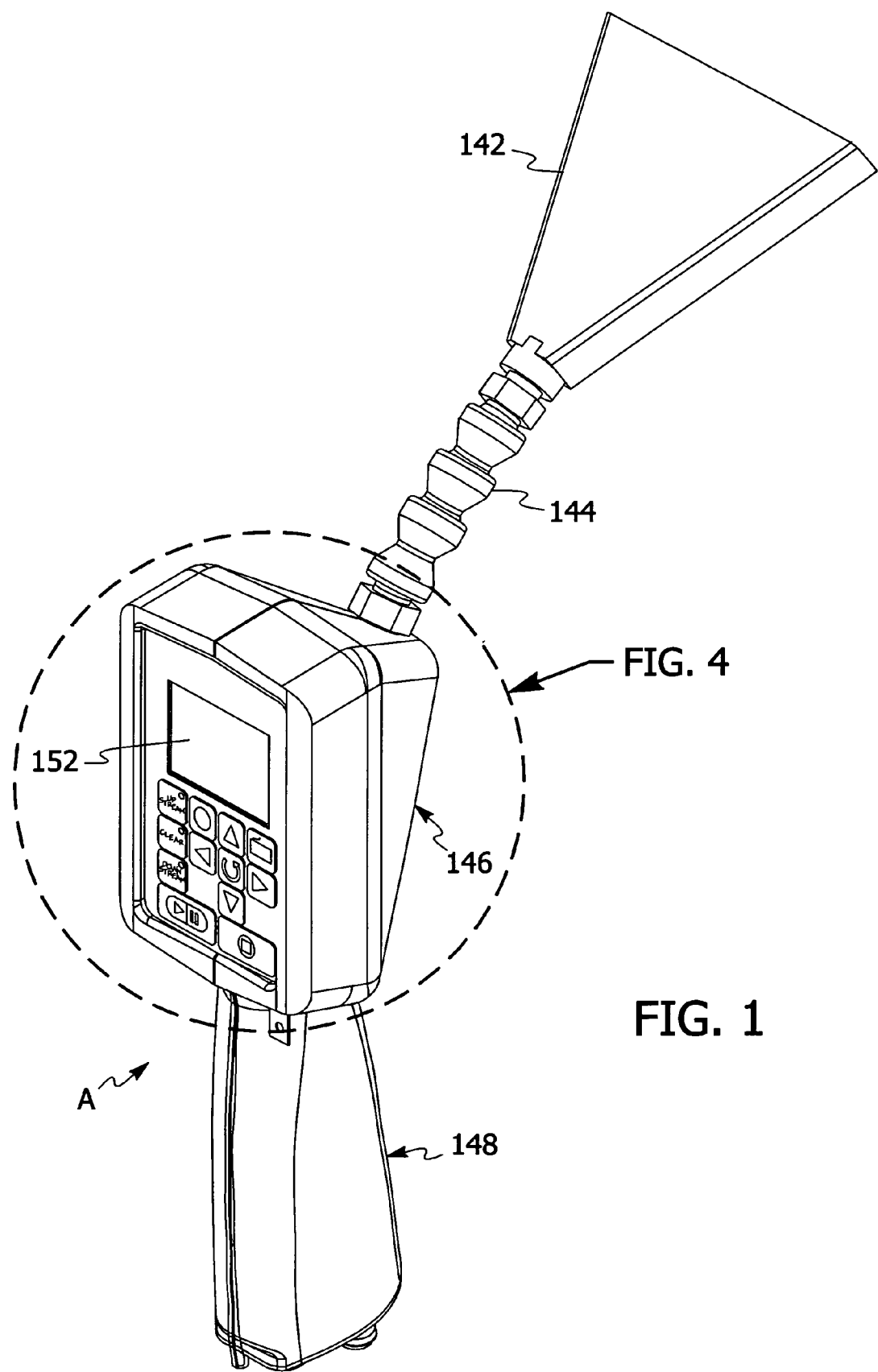
FIG. 1 is a perspective view illustrating a most preferred form of probe.
Figure 2:
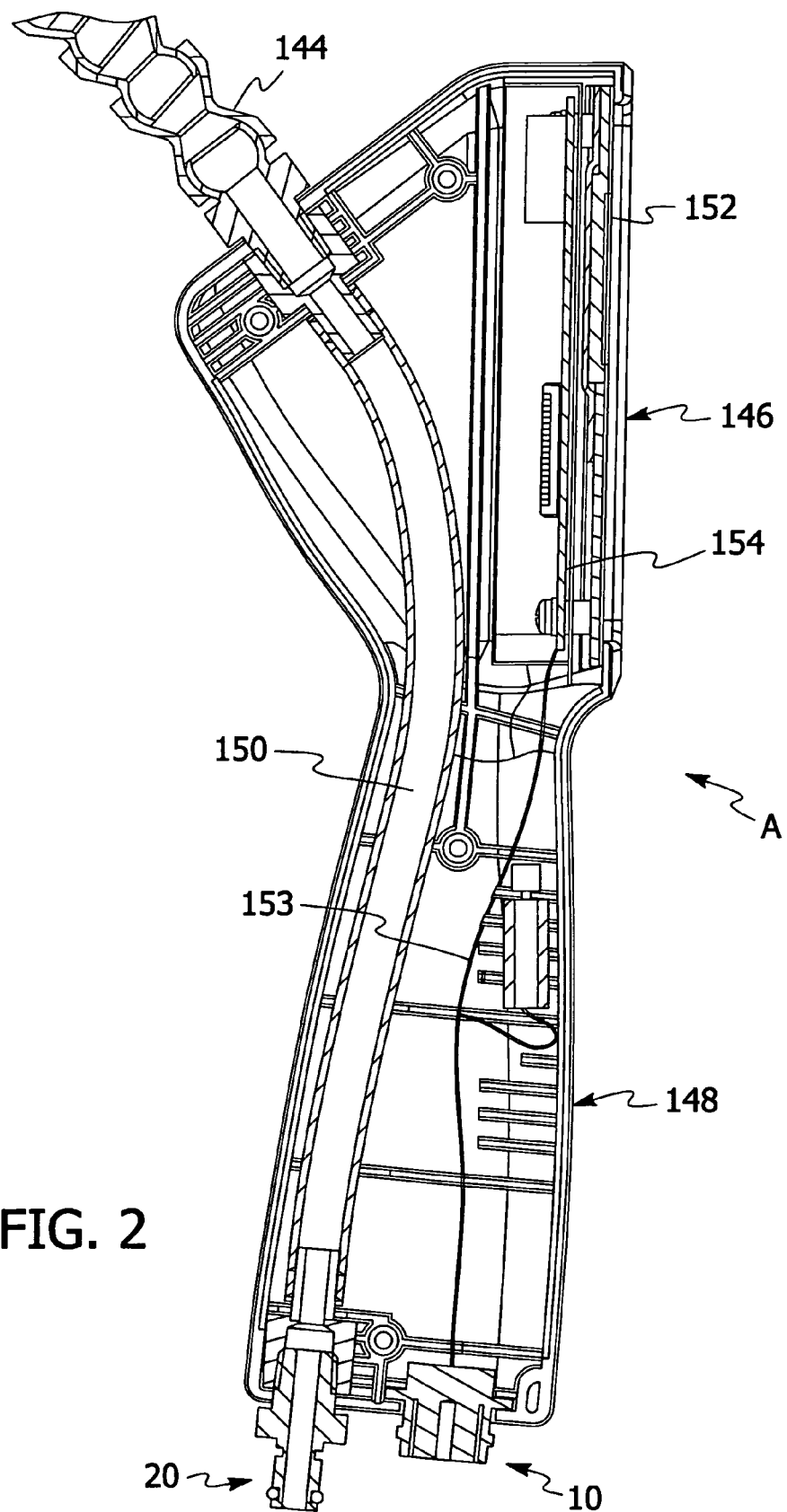
FIG. 2 is a fragmentary cross-sectional view of the preferred probe illustrated in FIG. 1.
Figure 3:
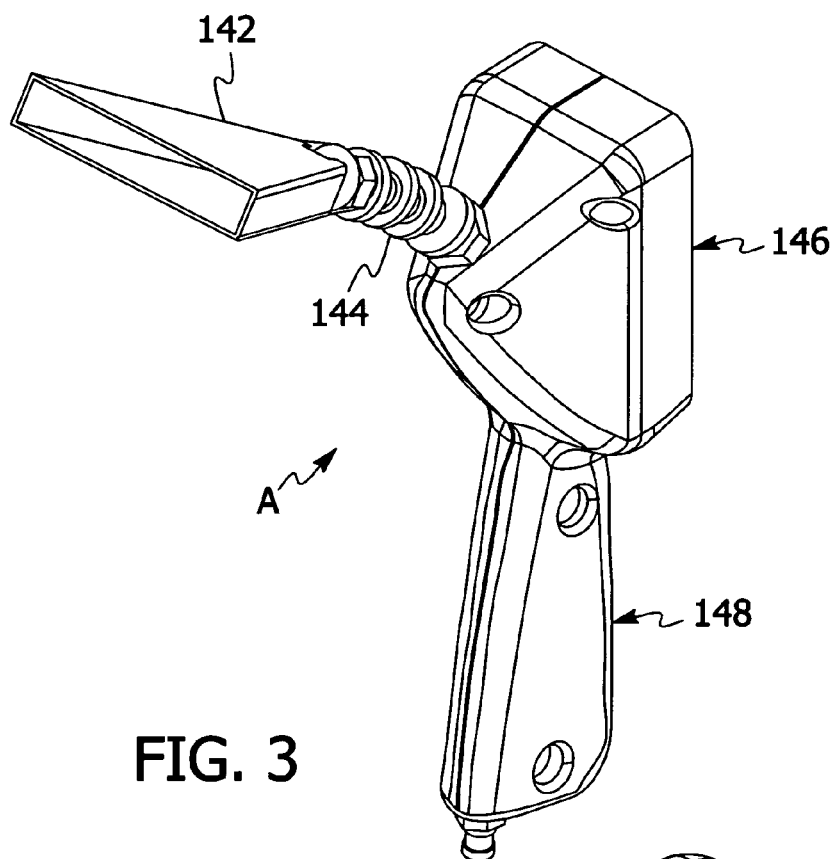
FIG. 3 is a perspective view illustrating the opposing side of the most preferred form of probe depicted in FIG. 1.

Main body 146 includes a display screen 152, a circuit board 154 having a microprocessor and a plurality of control members. An electrical connector 153 connects the circuit board 154 to electrical connection port 10 extending from the bottom of handle 148. As seen in FIGS. 2, 5 and 15, electrical connectors 2 and 153 connect circuit board 154 to main circuit board L in base unit C. Probe A has many of the same control members as the base unit. The same reference numerals have been used to designate the same control members. Referring to FIG. 4, main body 146 includes control members 28, 30, 36, 38, 40, 42, 44, 46, 48, 52 and 54.

By depressing control member 28, solenoid valve 64 will be opened or activated and solenoid valves 62 and 66 will remain closed or deactivated. This will cause vacuum pump E to pull an upstream test sample through port 22, manifold 60, photometer G, exhaust filter N, flow meter assembly H and vacuum pump E. The test sample is exhausted from base unit C after passing through pump E. Notably, any aerosol is filtered out of the test sample by filter N prior to the test sample being returned to the surrounding environment.

By depressing control member 30, solenoid valve 62 will be opened or activated and solenoid valves 64 and 66 will remain closed or deactivated. This will cause vacuum pump E to pull clean air from filter M through manifold 60, photometer G, exhaust filter N, flow meter assembly H and vacuum pump E. The clean air is exhausted from base unit C after passing through pump E. Notably, any residual aerosol that may have been in manifold 60 prior to activation of valve 62 will be removed from the manifold 60 along with the clean air. Any residual aerosol will be filtered out by filter N.

By depressing control member 32 of probe A, solenoid valve 66 will be opened or activated and solenoid valves 62 and 64 will remain closed or deactivated. This will cause vacuum pump E to pull an upstream test sample through nozzle 142, arm 142, conduit 150, conduit 12, port 18, manifold 60, photometer G, exhaust filter N, flow meter assembly H and vacuum pump E. The test sample is exhausted from base unit C after passing through pump E. Notably, any aerosol is filtered out of the test sample by filter N prior to the test sample being returned to the surrounding environment.

The preferred filter testing system is configured such that clean air solenoid valve 62 is automatically activated for a brief period when an operator changes from testing an upstream sample to testing a downstream sample as well as when an operator changes from testing a downstream sample to testing an upstream sample so that any residual aerosol in manifold 60 from a prior test may be readily exhausted from the manifold before analysis is performed on the current test sample. The automatic activation of the solenoid valve 62 occurs whether an operator uses probe A or base unit C to switch between upstream and downstream test sampling.

Upon depression of control member 36, an alpha-numeric key pad will be displayed on screen 152. Control member 38 allows an operator to disable the audible alarm feature of the filter test system if desired from the probe A without the operator manipulating any control member on base unit C, i.e., by depressing control member 38 on probe A, the audible alarm that would typically sound when a filter has failed the test will be disabled.

Cursor directional control members 40, 42, 44 and 46 allow an operator to move a cursor left, right, up and down on screen 152, respectively. Control member 48 is also provided on main body 146 and acts as an enter key. Using control members 40 through 48, an operator may readily navigate through the alpha-numeric key board and the menu to enter information regarding a filter being tested or select various features available in the menu without the operator manipulating any control member on base unit C.

By pressing the arrow portion of control member 52, the filter testing system will perform the test selected by the operator, again without the operator manipulating any control member on base unit C. By pressing the two parallel vertical lines portion of control member 52, the operator can pause the test without manipulating any control member on base unit C. To continue the filter test, the operator need only depress the arrow portion of control member 52 on probe A. By depressing control member 54, the test is stopped.

The filter system preferably includes a sensor for sensing when probe A is connected to base unit C. The sensor may be cooperating chips, one on main circuit board L and one on circuit board 154. The chips may take the form of an RS232 transceiver. The chip on main circuit board sends out RS232 data every few seconds to ascertain if probe A has been connected to base unit C. Once probe A is connected to base unit C, the probe provides a response to the query informing the base unit that probe A is connected. As explained in more detail below, the preferred form of the present invention is configured to prevent an operator from using signal noise suppression on a downstream test sample once probe A is connected to base unit C to avoid the possibility of masking a leak in a filter being tested. It will be readily appreciated that other operating parameters other than signal noise suppression of the downstream test sample may be altered once the filter test system detects that probe A is connected to base unit C.

The preferred form of filter test system is configured to check the variability of aerosol provided by an aerosol generator upstream of the filter being tested. When base unit C starts up, a "zero" reading is automatically performed to create a baseline for the measurement. During the "zero" reading, the clear air solenoid valve 62 is open and the upstream and downstream solenoid valves 64 and 66, respectively, are closed. This causes clean air to be drawn in and directed through the system as illustrated in FIG. 14. The flow is adjusted to 1 CFM and the voltage response is read from photometer G for 10 seconds. The data collected from the 10 second measurement is averaged and the standard deviation is calculated. If the standard deviation exceeds 0.0002 volts the zero reading is performed again. This process preferably repeats 2 more times. After the third attempt, the user will be asked if they want to proceed with the unstable zero reading or shutdown the machine. The filter test system may be configured to allow the user to select from a menu the "zero" reading test.

The preferred filter testing system allows an operator to select from the operating menu a procedure that will create a 100% reference for the upstream aerosol. When the user selects this option from the menu displayed on either probe A or base unit C, the clear air solenoid valve 62 and downstream solenoid valve 66 are closed and the upstream solenoid valve 64 is opened or activated. This causes an upstream aerosol test sample to pass through base unit C in the manner illustrated in FIG. 14. A 10 second sample is collected and averaged. The variance is also calculated from the sample. If the variance is more than 30 the user is warned that the upstream aerosol is unstable and asked if they want to continue. If the operator elects to continue, the operator can perform signal noise suppression on the upstream test sample. Specifically, the user can suppress the aerosol variation displayed to the screen on probe A and base unit C when measuring the upstream concentration. This function allows the user to choose between a 30 through 120 point moving average that stabilizes the reading. It should be noted that an operator can readily analyze an upstream test sample at any time by depressing control member 28.

The preferred filter testing system allows the user to perform downstream signal noise suppression. Specifically, the user can suppress the aerosol variation displayed to the screen of probe A and base unit C when measuring the downstream concentration. This function allows the user to choose between a 10, 20, 30 point moving average that stabilizes the reading. However, when probe A is connected to the base unit C, the preferred filter testing system is configured to prevent the operator from performing downstream signal noise suppression.

Standard deviation (Stdev) and Variance (Var) are preferably ascertained using the following formulas:

$$\text{Var} = \sum_{i=0}^{n=10} (\bar{x} - x_i)^2$$

$$Stdev = \sqrt{\frac{\text{Var}}{n}}$$

where n is the number of samples, $x_i$ is the voltage reading at time i and $\bar{x}$ is the average of n voltage readings.

While this invention has been described as having a preferred design, it is understood that the preferred design can be further modified or adapted following in general the principles of the invention and including but not limited to such departures from the present invention as come within the known or customary practice in the art to which the invention pertains. The claims are not limited to the preferred embodiment and have been written to preclude such a narrow construction using the principles of claim differentiation.

We claim:

1. An apparatus for testing a filter in situ, said apparatus comprising:

(a) a base unit being configured to operate in at least a first mode and a second mode, said base unit having an upstream sample port and a downstream sample port, in the first mode said base unit being configured to perform a first test on an upstream test sample taken upstream of a filter being tested and in the second mode said base unit being configured to perform a second test on a downstream test sample taken downstream of a filter being tested; and, (b) a handheld probe operably connected to said downstream sample port of said base unit, said handheld probe being configured to be deployed adjacent the filter being tested while the filter being tested is located in a normal operating position, said handheld probe having a first activation portion and a second activation portion, upon activation of said first activation portion by a user the downstream test sample is drawn through said handheld probe and said downstream sample port of said base unit and upon activation by a user of the second activation portion the upstream test sample is drawn through an upstream conduit and said upstream sample port of said base unit, said upstream conduit being connected at a first end to said upstream sample port of said base unit and a second end of said upstream conduit being positioned upstream of the filter being tested and wherein no potion of the upstream test sample passes through said handheld probe.

2. An apparatus as set forth in claim 1, wherein:

(a) in said first mode said base unit is configured to receive and analyze an upstream test sample taken upstream of a filter being tested, in said second mode said base unit is configured to receive and analyze a downstream test sample taken downstream of a filter being tested; and, (b) said base unit includes a photometer for analyzing the upstream test sample and the downstream test sample.

3. An apparatus as set forth in claim 1, wherein:

(a) said handheld probe includes a display screen and a third activation portion which when activated by a person holding the handheld probe displays an interactive keyboard on the display screen that an operator can interact with to enter information.

4. An apparatus as set forth in claim 3, wherein:

(a) said handheld probe includes a fourth activation portion which when activated by a user places the base unit in a pause mode in which filter testing is temporarily suspended; and, said handheld probe includes a fifth activation portion which when activated by a user places the base unit in a clear mode in which residual test sample in said base unit is exhausted from said base unit.

5. An apparatus as set forth in claim 4, wherein:

(a) said first activation portion, said second activation portion, said third activation portion, said fourth activation portion and said fifth activation portion of said handheld probe are disposed below said display screen.

6. An apparatus as set forth in claim 5, wherein:

(a) said handheld probe further includes a test sample collection head and a handle, said display screen is disposed between said test sample collection head and said handle.

7. An apparatus as set forth in claim 6, further including:
(a) at least a first conduit for electrically coupling said handheld probe to said base unit, said at least a first conduit is connected to a bottom of said handle of said handheld probe; and,
(b) a downstream conduit for directing the downstream test sample received by said handheld probe to said base unit for analysis.

8. An apparatus for testing a filter in situ, said apparatus comprising:
(a) an in situ filter test unit for analyzing a test sample having an upstream sample port and a downstream sample port, said in situ filter test unit being configured to operate in at least a first operating mode and a second operating mode, in the first operating mode said in situ filter test unit being configured to receive an upstream test sample taken upstream of a filter being tested, in the second operating mode said in situ filter test unit being configured to receive a downstream test sample taken downstream of a filter being tested, said in situ filter test unit further being configured to analyze at least one of the downstream test sample and the upstream test sample to determine if the filter being tested is operating satisfactorily without removing the filter being tested from a normal operating position;
(b) a handheld probe operably connected to said downstream sample port of said in situ filter test unit, said handheld probe being configured to be deployed adjacent the filter being tested while the filter being tested is located in a normal operating position, said handheld probe having a first activation portion and a second activation portion, upon activation of said first activation portion by a user the downstream test sample is drawn through said handheld probe and said downstream sample port of said base unit and upon activation by a user of the second activation portion the upstream test sample is drawn through an upstream conduit and said upstream sample port of said base unit, said upstream conduit being connected at a first end to said upstream sample port of said base unit and a second end of said upstream conduit being positioned upstream of the filter being tested and wherein no potion of the upstream test sample passes through said handheld probe; and,
(c) said in situ filter test unit being configured to automatically initiate a clear mode in which residual test sample in said in situ filter test unit is exhausted from said in situ filter test unit when a user activates either said first activation portion or said second activation portion.

9. An apparatus as set forth in claim 8, wherein:
(a) said in situ filter test unit includes a manifold having at least three entry ports and at least one discharge port, said at least three entry ports include an upstream test sample entry port, a downstream test sample entry port and a clean air entry port; and,
(b) said in situ filter test unit further includes valve means for selectively opening said upstream test sample entry port, said downstream test sample entry port and said clean air entry port.

10. An apparatus as set forth in claim 9, wherein:
(a) said in situ filter test unit includes a base unit having a photometer, said manifold and valve means being disposed in said base unit, said handheld probe being electrically coupled to said base unit to activate said valve means to open said upstream test sample entry port when the user activates said second activation portion and open said downstream test sample entry port when the user activates said first activation portion; and
(b) said handheld probe further includes a third activation portion which when activated by the user causes the clear air entry port to open.

11. An apparatus as set forth in claim 10, wherein:
(a) said valve means includes a plurality of solenoid valves connected to said manifold.

12. An apparatus as set forth in claim 11, wherein:
(a) said valve means includes three solenoid valves, each of the three solenoid valves are connected to one of said upstream test sample entry port, said downstream test sample entry port and said clean air entry port to open and close the corresponding entry port.

13. An apparatus as set forth in claim 12, wherein:
(a) said base unit is configured to automatically open the solenoid valve connected to said clean air entry port upon at least one of the following conditions occurring: (i) said upstream test sample entry port goes from an open state to a closed state; and, (ii) said downstream test sample entry port goes from an open state to a closed state.

14. An apparatus as set forth in claim 12, wherein:
(a) said base unit is configured to operate in an upstream test sample mode in which said base unit analyzes a test sample taken upstream of the filter being tested and a downstream test sample mode in which said base unit analyzes a test sample taken downstream of the filter being tested, said base unit is configured to automatically open the solenoid valve connected to said clean air entry port when said base unit changes between said upstream test sample mode and downstream test sample mode such that if the base unit is operating in one of the upstream and said downstream test sample modes and is manipulated to act in the other of the upstream and downstream test sample modes said clean air entry port is opened to exhaust residual test sample in the base unit prior to operating said base unit in the other of the upstream and downstream test sample modes.

15. An apparatus for testing a filter in situ, said apparatus comprising:
(a) a base unit for performing at least one test on a filter without the filter being removed from a normal operating position; and,
(b) a probe detachably connected to said base unit, said probe being configured to be deployed adjacent the filter being tested while the filter being tested is located in a normal operating position;
(c) a sensor for detecting whether said probe is connected to said base unit;
(d) said base unit being configured such that at least one functional aspect of said base unit being altered upon detection of said probe being connected to said base unit; and,
(e) means for performing noise suppression of a downstream sample and an upstream sample, said base unit being configured such that upon detection of said probe being connected to said base unit, noise suppression of a downstream sample cannot be performed.

16. An apparatus for testing a filter in situ, said apparatus comprising:
(a) a base unit being configured to operate in at least a first mode and a second mode, said base unit having an upstream sample port and a downstream sample port, in the first mode said base unit being configured to perform a first test on an upstream test sample taken upstream of a filter being tested and in the second mode said base unit being configured to perform a second test on a downstream test sample taken downstream of a filter being tested; and, (b) a handheld probe operably connected to said downstream sample port of said base unit, said handheld probe being configured to be deployed adjacent the filter being tested while the filter being tested is located in a normal operating position, said handheld probe having a first activation portion and a second activation portion, upon activation of said first activation portion by a user the downstream test sample is drawn through said handheld probe and said downstream sample port of said base unit and upon activation by a user of the second activation portion the upstream test sample is drawn through an upstream conduit and said upstream sample port of said base unit, said upstream conduit being connected at first end to said upstream sample port of said base unit and a second end of said upstream conduit being positioned upstream of the filter being tested and wherein no potion of the upstream test sample passes through said handheld probe; and, said handheld probe further including a third activation portion which when activated by a user places the base unit in a clear mode in which residual test sample in said base unit is exhausted from said base unit.

17. An apparatus as set forth in claim 16, wherein:
(a) said base unit is configured to allow a user to perform noise suppression on at least one of the downstream test sample and the upstream test sample, said base unit is further configured to allow the user to vary noise suppression, said base unit is configured to allow the user to perform noise suppression at least in part by data point moving average.

18. An apparatus as set forth in claim 17, wherein:
(a) said base test unit is configured to allow the user to select between a plurality of different data point moving averages to perform noise suppression.

19. An apparatus as set forth in claim 18, wherein:
(a) said base unit is configured to allow the user to select from 30 to 120 data point moving averages to perform noise suppression on an upstream aerosol test sample reading.

20. An apparatus as set forth in claim 19, wherein:
(a) said base unit is configured to allow the user to select from 10, 20 and 30 data point moving averages to perform noise suppression on a downstream aerosol test sample reading.

21. An apparatus as set forth in claim 17, wherein:
(a) said base unit is configured to prohibit noise suppression when said base unit is testing a downstream sample taken downstream of a filter being tested.

* * * * *